(12) United States Patent
Yusoff et al.

(10) Patent No.: US 6,939,957 B2
(45) Date of Patent: Sep. 6, 2005

(54) NUCLEOTIDE SEQUENCES OF THE NUCLEOCAPSID (NP) GENE OF A MALAYSIAN VELOGENIC NEWCASTLE DISEASE VIRUS STRAIN AF2240

(75) Inventors: Khatijah Mohd. Yusoff, Selangor (MY); Tan Wen Siang, Selangor (MY); Kho Chiew Ling, Selangor (MY)

(73) Assignee: Universiti Putra Malaysia, Selangor Darul Ehsan (MY)

( * ) Notice: Subject to any disclaimer, the term of this patent is extended or adjusted under 35 U.S.C. 154(b) by 614 days.

(21) Appl. No.: 09/970,851

(22) Filed: Oct. 4, 2001

(65) Prior Publication Data

US 2004/0170951 A1 Sep. 2, 2004

(30) Foreign Application Priority Data

Oct. 16, 2000 (MY) .................................... PI 2000 4837

(51) Int. Cl.[7] .......................... C07H 21/00; A61K 39/17
(52) U.S. Cl. ............................... 536/23.72; 424/214.1; 435/252.3; 435/320.1
(58) Field of Search ........................ 435/252.3, 320.1; 424/214.1; 536/23.72

(56) References Cited

PUBLICATIONS

Invitrogen® online catalog (http//:www.invitrogen.com), *E.coli* TOP10 product, catalog No. C4040–10, print–out from Oct. 13, 2004.*

Invitrogen® online catalog (http://www.invitrogen.com), plasmid pTrcHis2 product, catalog No. K4410–01, print–out from Oct. 13, 2004.*

Peeters et al., Journal of Virology, Jun. 1999, Rescue of Newcastle Disease Virus from Cloned cDNA, 73(6):5001–5009.*

Errington et al., Journal of General Virology, 1997, Assembly of recombinant Newcastle disease virus nucleocapsid protein into nucleocapsid–like structures is inhibited by the phosphoprotein, 78:2335–2339.*

Rahman et al., *Kajian Vet.* 8: 48–53 (1976).

Blaskovic and Styk *Virology* 1: 194–197 (1967).

Idris et al., *UNESCO Natl. Wkshp. on Promotion of Microbiol. in Malaysia*, 38 (1993).

Jemain, S.F.P., MS Thesis: "The Nucleotide Sequence of the Matrix (M) Protein Gene of Newcatle Disease Virus (NDV) Strain AF2240," Univ, Putra Malaysia (1999).

Lai, C.M., PhD Thesis: "A Study on a Velogenic Viscerotropic Newcastle Disease Virus in–vitro and in–vivo," Univ. Putra Malaysia (1985).

Salih et al., *J. Biochem, Mol. Biol., and Biophys.* 4: 51–57 (2000).

Tan et al., *DNA Sequence* 6: 47–50 (1995).

EMBL GenBank accession No. X79092.

EMBL GenBank accession No. AF048763.

EMBL GenBank accession No. AF060563.

EMBL GenBank accession No. AF284646.

EMBL GenBank accession No. AF284647.

Invitrogen website page containing genotype of *E. coli* TOP10 Cells (Nov. 11, 2004) https://catalog.invitrogen.com.

* cited by examiner

*Primary Examiner*—James Housel
*Assistant Examiner*—Stacy B. Chen
(74) *Attorney, Agent, or Firm*—Wolf, Greenfield & Sacks, P.C.

(57) ABSTRACT

The present invention relates to nucleotide sequences encoding the nucleocapsid (NP) protein and phosphoprotein (P) of Newcastle disease virus (NDV) and the production of the corresponding proteins with recombinant plasmids bearing the nucleotide sequences in *Escherichia coli*.

7 Claims, 2 Drawing Sheets

Detection of NP protein with anti-NDV chicken serum lanes:
1: Molecular mass standards expressed in kDa
2 & 3: NP fusion protein
4 & 5: NP non-fusion protein
6: NDV

Figure 1

Detection of P fusion protein with the anti-*Myc* monoclonal antibody lanes:
1: Cells containing the recombinant P fusion plasmid after being induced with IPTG for 5 h
2: Cells containing the recombinant P fusion plasmid after being induced with IPTG for 3 h
3: Cells containing the recombinant P fusion plasmid after being induced with IPTG for 1 h
4: Cells containing the recombinant P fusion plasmid before being induced with IPTG
5: Cells harbouring empty vector
6: Molecular mass standards expressed in kDa Detection of P non-fusion protein with anti-NDV chicken serum lanes:
1: Molecular mass standards expressed in kDa
2: Cells harbouring empty vector
3: Cells containing the recombinant P non-fusion plasmid before being induced with IPTG
4: Cells containing the recombinant P non-fusion plasmid after being induced with IPTG for 2 h
5: Cells containing the recombinant P non-fusion plasmid after being induced with IPTG for 4 h
6: Cells containing the recombinant P non-fusion plasmid after being induced with IPTG for 6 h

Figure 2

NUCLEOTIDE SEQUENCES OF THE NUCLEOCAPSID (NP) GENE OF A MALAYSIAN VELOGENIC NEWCASTLE DISEASE VIRUS STRAIN AF2240

FIELD OF THE INVENTION

The present invention relates to nucleotide sequences encoding the nucleocapsid (NP) protein and phosphoprotein (P) of Newcastle disease virus (NDV) strain AF2240, and the production of the corresponding proteins with recombinant plasmids bearing the nucleotide sequences in *Escherichia coli*.

DESCRIPTION OF THE PRIOR ART

Newcastle disease virus (NDV) is the prototype of avian paramyxovirus, which causes a highly contagious disease known as Newcastle disease (ND) in many avian species. This disease is of great economic importance requiring control by vaccination or quarantine with slaughter of all birds in confirmed outbreaks, resulting in substantial losses in the poultry industry worldwide. Therefore, development of an improved vaccine and also a rapid and sensitive diagnostic test are greatly desired by the poultry industry.

A Malaysian heat resistant NDV strain AF2240, which causes 100% mortality in susceptible chicken flocks has been reported by Abdul Rahman et al. (1976) and Lai, C. M. (1985). Further studies by Idris et al. (1993) revealed that the thermostabilities of haemagglutination and neuraminidase activities of this AF2240 strain were found to be higher than those of other strains. The basis giving rise to these unique features is still unknown. However a comprehensive understanding of the viral proteins would provide some solutions and useful information for the development of heat stable recombinant vaccines and diagnostic tests.

The genome of NDV is a linear, non-segmented, single-stranded negative sense RNA with a molecular weight of 5.2–5.7×10$^6$ Daltons, or approximately 15,000 bases which encodes six main structural proteins. The genomic RNA is associated with the nucleocapsid (NP), phosphoprotein (P) and large (L) proteins. These macromolecules form the transcriptive complex of the virus, which in turn is surrounded by a lipid bilayer membrane derived from the host cell. Embedded in the membrane are the haemagglutinin-neuraminidase (HN) and fusion (F) glycoproteins. Beneath the lipid bilayer is a shell of protein known as the matrix (M) protein, which is believed to interact with the transcriptive complex. The HN and F glycoproteins are associated with the host cell receptor during infection. The NP encapsidates the viral RNA together with the L protein which is thought to be the transcriptase, and a P protein with an unknown reason.

The genes encoding for the HN (EMBL/Gen Bank/DDBJ accession No.X79092), F (EMBL/Gen Bank/DDBJ accession No.AFO48763) and M (EMBL/Gen Bank/DDBJ accession No. AF060563) proteins of the NDV strain AF2240 have been completely sequenced by Tan et al. (1995), Salih et al. (2000) and Jemain, S. F. P. (1999) respectively. From the HN gene sequence of strain AF2240, it was quite clear that this strain is different from he other published NDV strains. The HN protein lacked the Arg (403) residue and contained 581 amino acids. At the time when the project was initiated, there was no information available on the coding sequences for the NP and P proteins of NDV strain AF2240. Therefore it remained a problem to prepare cDNA for the cloning of the NP and P genes of NDV.

The inventors have now successfully determined the nucleotide sequences encoding the NP and P proteins of NDV strain AF2240. The accession numbers for the genes encoding the NP and P proteins are EMBL/Gen Bank/DDBJ No. AF284646 and AF284647 respectively. The inventors had discovered that the proteins, in either non-fusion or fusion forms bearing the myc epitope and six residues of His at their carboxyl terminal end could be successfully produced in *E. coli* by means of recombinant DNA technologies. The NP and P proteins were expressed to a substantial level in the bacteria and can be recognised by chicken anti-NDV serum.

SUMMARY OF THE INVENTION

The present invention provides nucleotides encoding the full length NP and P polypeptides of Newcastle disease virus strain AF2240. Whereas the genome of NDV is of length approximately 15,000 nucleotides, it has been determined, by this invention, that the portion coding for the NP polypeptide is approximately 1470 nucleotides long and the portion that codes for the P polypeptide is approximately 1188 nucleotides long. Accordingly, one aspect of the present invention provides for the coding regions of the nucleocapsid (NP) and phosphoprotein (P) genes of Newcastle disease virus strain AF2240. Both the nucleotide sequences are as listed below:

```
                     NP coding region (SEQ ID NO: 1)

10         20         30         40         50         60
ATGTCTTCCG TATTCGATGA ATACGAGCAG CTCCTCGCTG CTCAGACTCG CCCCAATGGA 70         80         90        100        110        120
GCTCACGGAG GGGGAGAGAG AGGGAGCACT TTAAGAGTTG AGGTCCCAGT ATTCACTCTT 130        140        150        160        170        180
AACAGTGACG ATCCAGAAGA TAGATGGAAT TTTGCGGTAT TCTGTCTTCG GATTGCTGTT 190        200        210        220        230        240
AGCGAGGACG CCAACAAACC GCTCAGGCAA GGTGCTCTCA TATCCCTCCT GTGCTCCCAT 250        260        270        280        290        300
TCTCAAGTGA TGAGGAACCA TGTTGCCCTT GCAGGAAAAC AGAATGAGGC TACACTGACT 310        320        330        340        350        360
GTTCTTGAGA TCGATGGTTT TACCAGCAGC GTGCCTCAGT TCAACAACAG GAGTGGGGTG
```

-continued

|     |     |     |     |     |     |
| --- | --- | --- | --- | --- | --- |
| 370 | 380 | 390 | 400 | 410 | 420 |
| TCTGAGGAGA | GAGCACAGAG | ATTCATGGTG | ATAGCAGGGT | CTCTCCCTCG | GGCGTCCACT |
| 430 | 440 | 450 | 460 | 470 | 480 |
| AACGGTACTC | CGTTCGTCAC | GGCTGGGGTT | GAAGATGATG | CACCAGAAGA | TATCACTGAT |
| 490 | 500 | 510 | 520 | 530 | 540 |
| ACTCTGGAAA | GAATCCTGTC | TATCCAGGCT | CAGGTATGGG | TCACAGTAGC | GAAGGCCATG |
| 550 | 560 | 570 | 580 | 590 | 600 |
| ACTGCATATG | AGACAGCAGA | TGAGTCGGAA | ACAAGAAGAA | TCAATAAGTA | CATGCAGCAA |
| 610 | 620 | 630 | 640 | 650 | 660 |
| GGCAGAGTCC | AGAAGAAGTA | CATCCTCCAC | CCTGTATGCA | GGAGTGCAAT | TCAACTCACA |
| 670 | 680 | 690 | 700 | 710 | 720 |
| ATCAGACATT | CTCTGGCAGT | CCGCATTTTC | TTAGTTAGCG | AGCTTAAGAG | AGGCCGCAAT |
| 730 | 740 | 750 | 760 | 770 | 780 |
| ACGGCAGGTG | GGAGCTCCAC | GTATTACAAC | TTAGTAGGGG | ATGTAGACTC | ATACATCAGG |
| 790 | 800 | 810 | 820 | 830 | 840 |
| AACACCGGAC | TTACTGCATT | CTTCCTTACA | CTCAAATATG | GAATTAATAC | CAAGACATCA |
| 850 | 860 | 870 | 880 | 890 | 900 |
| GCCCTAGCAC | TCAGCAGCCT | CACAGGCGAT | ATCCAAAAGA | TGAAGCAGCT | CATGCGTTTA |
| 910 | 920 | 930 | 940 | 950 | 960 |
| TATCGGATGA | AGGGAGAAAA | TGCGCCGTAC | ATGACATTGC | TAGGTGACAG | TGATCAGATG |
| 970 | 980 | 990 | 1000 | 1010 | 1020 |
| AGCTTTGCAC | CGGCTGAGTA | TGCACAGCTT | TATTCTTTTG | CCATGGGCAT | GGCATCAGTC |
| 1030 | 1040 | 1050 | 1060 | 1070 | 1080 |
| TTAGATAAAG | GAACTGGCAA | ATACCAATTC | GCCAGAGACT | TCATGAGCAC | ATCATTCTGG |
| 1090 | 1100 | 1110 | 1120 | 1130 | 1140 |
| AGACTCGGGG | TGGAGTATGC | TCAGGCTCAG | GGGAGTAGCA | TCAACGAACA | CATGGCTGCT |
| 1150 | 1160 | 1170 | 1180 | 1190 | 1200 |
| GAGCTAAAC | TAACCCCGGC | AGCAAGAAGG | GGCCTGGCAG | CTGCTGCCCA | ACGAGTGTCT |
| 1210 | 1220 | 1230 | 1240 | 1250 | 1260 |
| GAGGAAACTG | GCAGCGTGGA | TATTCCTACT | CAACAAGCCG | GGGTCCTCAC | TGGGCTCAGC |
| 1270 | 1280 | 1290 | 1300 | 1310 | 1320 |
| GATGGAGGCC | CCCGAGCCTC | TCAGGGTGGA | TCGAACAAGT | CGCAAGGGCA | ACCAGATGCC |
| 1330 | 1340 | 1350 | 1360 | 1370 | 1380 |
| GGAGATGGGG | AGACCCAATT | CTTGGATTTG | ATGAGAGCAG | TGGCGAACAG | CATGCGAGAA |
| 1390 | 1400 | 1410 | 1420 | 1430 | 1440 |
| GCGCCAAACT | CCGCACAGAG | CACCACCCAC | CCGGAACCCC | CCCCGACTCC | CGGGCCATCA |
| 1450 | 1460 | 1470 | 1480 | 1490 | 1500 |
| CAAGATAACG | ACACCGACTG | GGGGTATTGA | .......... | .......... | .......... |

P gene coding region (SEQ ID NO: 2)

|     |     |     |     |     |     |
| --- | --- | --- | --- | --- | --- |
| 10 | 20 | 30 | 40 | 50 | 60 |
| ATGGCCACCT | TTACAGATGC | GGAGATAGAT | GATATATTTG | AGACCAGTGG | AACTGTCATT |
| 70 | 80 | 90 | 100 | 110 | 120 |
| GACAGCATAA | TTACGGCCCA | GGGTAAATCA | GCAGAGACTG | TCGGAAGGAG | CGCAATCCCA |
| 130 | 140 | 150 | 160 | 170 | 180 |
| CAAGGCAAGA | CCAAAGCGCT | GAGCATAGCA | TGGGAGAAGC | ATGGGAGCAT | CCAACCATCC |
| 190 | 200 | 210 | 220 | 230 | 240 |
| ACCAGCCAGG | ACAACCCCGA | CCAACAGGAT | AGACCAGACA | AACAGCTATC | CACACCTGAG |
| 250 | 260 | 270 | 280 | 290 | 300 |
| CAGGCGACCC | CACACAACAG | CTCGCCAGCC | ACATCCGCCG | AACCGCTCCC | CACTCAGGCC |
| 310 | 320 | 330 | 340 | 350 | 360 |
| GCAGGTGAGG | CCGGCGACAC | ACAGCTCAAG | ACCGGAGCAA | GCAACTCTCT | TCTGTCTATG |

-continued

```
          370        380        390        400        410        420
     CTCGACAAGC TGAGCAATAA ACCATCTAAT GCTAAAAAGG GCCCATGGTC GAGTCCCCAG 430        440        450        460        470        480
     GAAGGATATC ATCAACCTCC GACCCAACAA CATGGGGATC AGCCGAACCG CGGAAACAGC 490        500        510        520        530        540
     CAGGAGAGGC TGCGGCACCA AGCCAAGGCC GCCCCTGGAA GCCGGGGCAC AGACGCGAGC 550        560        570        580        590        600
     ACAGCATATC ATGGACAATG GAAGGAGTCA CAACTATCAG CTGGTGCAAC CCCTCATGTG 610        620        630        640        650        660
     CTCCAATCAG GGCAGAGCCA AGACAGTACT CCTGTACCTG TGGATCATGT CCAGCCACCT 670        680        690        700        710        720
     GTCGACTTTG TGCAGGCGAT GATGACTATG ATGGAGGCGT TATCACAGAA GGTAAGTAAA 730        740        750        760        770        780
     GTCGACTATC AGCTAGACCT AGTCTTAAAG CAGACATCCT CCATCCCTAT GATGCGGTCT 790        800        810        820        830        840
     GAAATCCAAC AGCTAAAAAC ATCTGTTGCG GTCATGGAAG CTAATTTAGG CATGATGAAA 850        860        870        880        890        900
     ATTCTGGACC CTGGTTGTGC TAACATTTCA TCCTTAAGTG ATCTGCGGGC AGTCGCCCGG 910        920        930        940        950        960
     TCCCACCCAG TTTTAATTTC AGGCCCCGGA GATCCGTCCC CCTACGTGAC ACAAGGGGGT 970        980        990       1000       1010       1020
     GAGATGACAC TCAATAAACT CTCACAACCA GTACAACACC CTTCCGAGTT AATTAAATCT 1030       1040       1050       1060       1070       1080
     GCCACAGCGG GCGGACCTGA TATGGGAGTG GAAAAGGACA CTGTCCGTGC ATTGATCACC 1090       1100       1110       1120       1130       1140
     TCGCGCCCGA TGCATCCAAG CTCCTCAGCT AAGCTCCTGA GTAAGCTGGA TGCAGCCGGG 1150       1160       1170       1180       1190       1200
     TCGATTGAAG AGATCAGAAA GATCAAGCGC CTTGCACTAA ATGGCTAA.. ..........
```

Further, the present invention provides the amino acid sequences of both the NP and P proteins as listed below:

NP gene (SEQ ID NO: 1): amino acid sequence (SEQ ID NO: 3)

| NP gene (SEQ ID NO: 1): amino acid sequence (SEQ ID NO: 3) | | | | | | | | | | | | | | | | |
|---|---|---|---|---|---|---|---|---|---|---|---|---|---|---|---|---|
| 1 | M | S | S | V | F | D | E | Y | E | Q | L | L | A | A | Q | T | 16 |
|  | ATG | TCT | TCC | GTA | TTC | GAT | GAA | TAC | GAG | CAG | CTC | CTC | GCT | GCT | CAG | ACT |  |
|  | 1 |  | 10 |  | 20 |  | 30 |  |  | 40 |  |  |  |  |  |  |  |
| 17 | R | P | N | G | A | H | G | G | G | E | R | G | S | T | L | R | 32 |
|  | CGC | CCC | AAT | GGA | GCT | CAC | GGA | GGG | GGA | GAG | AGA | GGG | AGC | ACT | TTA | AGA |  |
|  | 50 |  |  | 60 |  |  | 70 |  |  | 80 |  |  | 90 |  |  |  |  |
| 33 | V | E | V | P | V | F | T | L | N | S | D | D | P | E | D | R | 48 |
|  | GTT | GAG | GTC | CCA | GTA | TTC | ACT | CTT | AAC | AGT | GAC | GAT | CCA | GAA | GAT | AGA |  |
|  |  | 100 |  |  | 110 |  |  | 120 |  |  | 130 |  |  | 140 |  |  |  |
| 49 | W | N | F | A | V | F | C | L | R | I | A | V | S | E | D | A | 64 |
|  | TGG | AAT | TTT | GCG | GTA | TTC | TGT | CTT | CGG | ATT | GCT | GTT | AGC | GAG | GAC | GCC |  |
|  |  | 150 |  |  | 160 |  |  | 170 |  |  | 180 |  |  | 190 |  |  |  |
| 65 | N | K | P | L | R | Q | G | A | L | I | S | L | L | C | S | H | 80 |
|  | AAC | AAA | CCG | CTC | AGG | CAA | GGT | GCT | CTC | ATA | TCC | CTC | CTG | TGC | TCC | CAT |  |
|  |  | 200 |  |  | 210 |  |  | 220 |  |  | 230 |  |  | 240 |  |  |  |
| 81 | S | Q | V | M | R | N | H | V | A | L | A | G | K | Q | N | E | 96 |
|  | TCT | CAA | GTG | ATG | AGG | AAC | CAT | GTT | GCC | CTT | GCA | GGA | AAA | CAG | AAT | GAG |  |
|  |  | 250 |  |  | 260 |  |  | 270 |  |  | 280 |  |  |  |  |  |  |

```
                              -continued

97  A   T   L   T   V   L   E   I   D   G   F   T   S   S   V   P   112
     GCT ACA CTG ACT GTT CTT GAG ATC GAT GGT TTT ACC AGC AGC GTG CCT
     290         300         310         320         330

113  G   F   N   N   R   S   G   V   S   E   E   R   A   Q   R   F   128
     CAG TTC AAC AAC AGG AGT GGG GTG TCT GAG GAG AGA GCA CAG AGA TTC
         340         350         360         370         380

129  M   V   I   A   G   S   L   P   R   A   C   S   N   G   T   P   144
     ATG GTG ATA GCA GGG TCT CTC CCT CGG GCG TGC AGT AAC GGT ACT CCG
             390         400         410         420         430

145  F   V   T   A   G   V   E   D   D   A   P   E   D   I   T   D   160
     TTC GTC ACG GCT GGG GTT GAA GAT GAT GCA CCA GAA GAT ATC ACT GAT
                 440         450         460         470         480

161  T   L   E   R   I   L   S   I   Q   A   Q   V   W   V   T   V   176
     ACT CTG GAA AGA ATC CTG TCT ATC CAG GCT CAG GTA TGG GTC ACA GTA
                     490         500         510         520

177  A   K   A   M   T   A   Y   E   T   A   D   E   S   E   T   R   192
     GCG AAG GCC ATG ACT GCA TAT GAG ACA GCA GAT GAG TCG GAA ACA AGA
     530         540         550         560         570

193  R   I   N   K   Y   M   Q   Q   G   R   V   Q   K   K   Y   I   208
     AGA ATC AAT AAG TAC ATG CAG CAA GGC AGA GTC CAG AAG AAG TAC ATC
         580         590         600         610         620

209  L   H   P   V   C   R   S   A   I   Q   L   T   I   R   H   S   224
     CTC CAC CCT GTA TGC AGG AGT GCA ATT CAA CTC ACA ATC AGA CAT TCT
             630         640         650         660         670

225  L   A   V   R   I   F   L   V   S   E   L   K   R   G   R   N   240
     CTG GCA GTC CGC ATT TTC TTA GTT AGC GAG CTT AAG AGA GGC CGC AAT
                 680         690         700         710         720

241  T   A   G   G   S   S   T   Y   Y   N   L   V   G   D   V   D   256
     ACG GCA GGT GGG AGC TCC ACG TAT TAC AAC TTA GTA GGG GAT GTA GAC
                     730         740         750         760

257  S   Y   I   R   N   T   G   L   T   A   F   F   L   T   L   K   272
     TCA TAC ATC AGG AAC ACC GGA CTT ACT GCA TTC TTC CTT ACA CTC AAA
     770         780         790         800         810

273  Y   G   I   N   T   K   T   S   A   L   A   L   S   S   L   T   288
     TAT GGA ATT AAT ACC AAG ACA TCA GCC CTA GCA CTC AGC AGC CTC ACA
         820         830         840         850         860

289  G   D   I   Q   K   M   K   Q   L   M   R   L   Y   R   M   K   304
     GGC GAT ATC CAA AAG ATG AAG CAG CTC ATG CGT TTA TAT CGG ATG AAG
             870         880         890         900         910

305  G   E   N   A   P   Y   M   T   L   L   G   D   S   D   Q   M   320
     GGA GAA ATT GCC CCG TAC ATG ACA TTG CTA GGT GAC AGT GAT CAG ATG
                 920         930         940         950         960

321  S   F   A   P   A   E   Y   A   Q   L   Y   S   F   A   M   G   336
     AGC TTT GCA CCG GCT GAG TAT GCA CAG CTT TAT TCT TTT GCC ATG GGC
                     970         980         990         1000

337  M   A   S   V   L   D   K   G   T   G   K   Y   Q   F   A   R   352
     ATG GCA TCA GTC TTA GAT AAA GGA ACT GGC AAA TAC CAA TTC GCC AGA
     1010        1020        1030        1040        1050

353  D   F   M   S   T   S   F   W   R   L   G   V   E   Y   A   Q   368
     GAC TTC ATG AGC ACA TCA TTC TGG AGA CTC GGG GTG GAG TAT GCT CAG
         1060        1070        1080        1090        1100

369  S   Q   G   S   S   I   N   E   D   M   A   A   E   L   K   L   384
     GCT CAG GGG AGT AGC ATC AAC GAA CAG ATG GCT GCT GAG CTA AAA CTA
             1110        1120        1130        1140        1150

385  T   P   A   A   R   R   G   L   A   A   A   G   R   V   S   400
     ACC CCG GCA GCA AGA AGG GGC CTG GCA GCT GCT GCC CAA CGA GTG TCT
                 1160        1170        1180        1190        1200
```

-continued

| | | | | | | | | | | | | | | | | | |
|---|---|---|---|---|---|---|---|---|---|---|---|---|---|---|---|---|---|
| 401 | E | E | T | G | S | V | D | I | P | T | Q | Q | A | G | V | L | 416 |
| | GAG | GAA | ACT | GGC | AGC | GTG | GAT | ATT | CCT | ACT | CAA | CAA | GCC | GGG | GTC | CTC | |
| | | | 1210 | | | 1220 | | | 1230 | | | 1240 | | | | | |

| 417 | T | G | L | S | D | G | G | P | R | A | S | Q | G | G | S | N | 432 |
| | ACT | GGG | CTC | AGC | GAT | GGA | GGC | CCC | CGA | GCC | TCT | CAG | GGT | GGA | TCG | AAC | |
| | 1250 | | | 1260 | | | 1270 | | | 1280 | | | 1290 | | | | |

| 433 | K | S | Q | G | Q | P | D | A | G | D | G | E | T | Q | F | L | 448 |
| | AAG | TCG | CAA | GGG | CAA | CCA | GAT | GCC | GGA | GAT | GGG | GAG | ACC | CAA | TTC | TTG | |
| | | 1300 | | | 1310 | | | 1320 | | | 1330 | | | 1340 | | | |

| 449 | D | L | M | R | A | V | A | N | S | M | R | E | A | P | N | S | 464 |
| | GAT | TTG | ATG | AGA | GCA | GTG | GCG | AAC | AGC | ATG | CGA | GAA | GCG | CCA | AAC | TCC | |
| | | 1350 | | | 1360 | | | 1370 | | | 1380 | | | 1390 | | | |

| 465 | A | Q | S | T | T | H | P | E | P | P | P | T | P | G | P | S | 480 |
| | GCA | CAG | AGC | ACC | ACC | CAC | CCG | GAA | CCC | CCC | CCG | ACT | CCC | GGG | CCA | TCC | |
| | | 1400 | | | 1410 | | | 1420 | | | 1430 | | | 1440 | | | |

| 481 | Q | D | N | D | T | D | W | G | Y | * | | | | | | | 490 |
| | CAA | GAT | AAC | GAC | ACC | GAC | TGG | GGG | TAT | TGA | | | | | | | |
| | | 1450 | | | 1460 | | | 1470 | | | | | | | | | |

| P gene: (SEQ ID NO: 2): amino acid sequence (SEQ ID NO: 4) |
|---|

| 1 | M | A | T | F | T | D | A | E | I | D | D | I | F | E | T | S | 16 |
| | ATG | GCC | ACC | TTT | ACA | GAT | GCG | GAG | ATA | GAT | GAT | ATA | TTT | GAG | ACC | AGT | |
| | 1 | | 10 | | | 20 | | | 30 | | | 40 | | | | | |

| 17 | G | T | V | I | D | S | I | I | T | A | Q | G | K | S | A | E | 32 |
| | GGA | ACT | GTC | ATT | GAC | AGC | ATA | ATT | ACG | GCC | CAG | GGT | AAA | TCA | GCA | GAG | |
| | 50 | | | 60 | | | 70 | | | 80 | | | 90 | | | | |

| 33 | T | V | G | R | S | A | I | P | Q | G | K | T | K | A | L | S | 48 |
| | ACT | GTC | GGA | AGG | AGC | GCA | ATC | CCA | CAA | GGC | AAG | ACC | AAA | GCG | CTG | AGC | |
| | | 100 | | | 110 | | | 120 | | | 130 | | | 140 | | | |

| 49 | I | A | W | E | K | H | G | S | I | Q | P | S | T | S | Q | D | 64 |
| | ATA | GCA | TGG | GAG | AAG | CAT | GGG | AGC | ATC | CAA | CCA | TCC | ACC | AGC | CAG | GAC | |
| | | 150 | | | 160 | | | 170 | | | 180 | | | 190 | | | |

| 65 | N | P | D | Q | Q | D | R | P | D | K | Q | L | S | T | P | E | 80 |
| | AAC | CCC | GAC | CAA | CAG | GAT | AGA | CCA | GAC | AAA | CAG | CTA | TCC | ACA | CCT | GAG | |
| | | | 200 | | | 210 | | | 220 | | | 230 | | | 240 | | |

| 81 | Q | A | T | P | H | N | S | S | P | A | T | S | A | E | P | L | 96 |
| | CAG | GCG | ACC | CCA | CAC | AAC | AGC | TCG | CCA | GCC | ACA | TCC | GCC | GAA | CCG | CTC | |
| | | | 250 | | | 260 | | | 270 | | | 280 | | | | | |

| 97 | P | T | Q | A | A | G | E | A | G | D | T | Q | L | K | T | G | 112 |
| | CCC | ACT | CAG | GCC | GCA | GGT | GAG | GCC | GGC | GAC | ACA | CAG | CTC | AAG | ACC | GGA | |
| | 290 | | | 300 | | | 310 | | | 320 | | | 330 | | | | |

| 113 | A | S | N | S | L | L | S | M | L | D | K | L | S | N | K | P | 128 |
| | GCA | AGC | AAC | TCT | CTT | CTG | TCT | ATG | CTC | GAC | AAG | CTG | AGC | AAT | AAA | CCA | |
| | | 340 | | | 350 | | | 360 | | | 370 | | | 380 | | | |

| 129 | S | N | A | K | K | G | P | W | S | S | P | Q | E | G | Y | H | 144 |
| | TCT | AAT | GCT | AAA | AAG | GGC | CCA | TGG | TCG | AGT | CCC | CAG | GAA | GGA | TAT | CAT | |
| | | 390 | | | 400 | | | 410 | | | 420 | | | 430 | | | |

| 145 | Q | P | P | T | Q | Q | H | C | D | Q | P | N | R | G | N | S | 160 |
| | CAA | CCT | CCG | ACC | CAA | CAA | CAT | GGG | GAT | CAG | CCG | AAC | CGC | GGA | AAC | AGC | |
| | | | 440 | | | 450 | | | 460 | | | 470 | | | 480 | | |

| 161 | Q | E | R | L | R | H | Q | A | K | A | A | P | G | S | R | G | 176 |
| | CAG | GAG | AGG | CTG | CGG | CAC | CAA | GCC | AAG | GCC | GCC | CCT | GGA | AGC | CGG | GGC | |
| | | | | 490 | | | 500 | | | 510 | | | 520 | | | | |

| 177 | T | D | A | S | T | A | Y | H | G | Q | W | K | E | S | Q | L | 192 |
| | ACA | GAC | GCG | AGC | ACA | GCA | TAT | CAT | GGA | CAA | TGG | AAG | GAG | TCA | CAA | CTA | |
| | | 530 | | | 540 | | | 550 | | | 560 | | | 570 | | | |

| 193 | S | A | G | A | T | P | H | V | L | Q | S | G | Q | S | G | D | 208 |
| | TCA | GCT | GGT | GCA | ACC | CCT | CAT | GTG | CTC | CAA | TCA | GGG | CAG | AGC | CAA | GAC | |
| | | 580 | | | 590 | | | 600 | | | 610 | | | 620 | | | |

-continued

```
209  S    T    P    V    P    V    D    H    V    Q    P    P    V    D    F    V    224
     AGT  ACT  CCT  GTA  CCT  GTG  GAT  CAT  GTC  CAG  CCA  CCT  GTC  GAC  TTT  GTG
          630            640            650            660            670

225  Q    A    M    M    T    M    M    E    A    L    S    Q    K    V    S    K    240
     CAG  GCG  ATG  ATG  ACT  ATG  ATG  GAG  GCG  TTA  TCA  CAG  AAG  GTA  AGT  AAA
          680            690            700            710            720

241  V    D    Y    Q    L    D    L    V    L    K    Q    T    S    S    I    P    256
     GTC  GAC  TAT  CAG  CTA  GAC  CTA  GTC  TTA  AAG  CAG  ACA  TCC  TCC  ATC  CCT
               730            740            750            760

257  M    M    R    S    E    I    Q    Q    L    K    T    S    V    A    V    M    272
     ATG  ATG  CGG  TCT  GAA  ATC  CAA  CAG  CTA  AAA  ACA  TCT  GTT  GCG  GTC  ATG
     770            780            790            800            810

273  E    A    N    L    G    M    M    K    I    L    D    P    G    C    A    N    288
     GAA  GCT  AAT  TTA  GGC  ATG  ATG  AAA  ATT  CTG  GAC  CCT  GGT  TGT  GCT  AAC
          820            830            840            850            860

289  I    S    S    L    S    D    L    R    A    V    A    R    S    H    P    V    304
     ATT  TCA  TCC  TTA  AGT  GAT  CTG  CGG  GCA  GTC  GCC  CGG  TCC  CAC  CCA  GTT
          870            880            890            900            910

305  L    I    S    G    P    G    D    P    S    P    Y    V    T    Q    G    G    320
     TTA  ATT  TCA  GGC  CCC  GGA  GAT  CCG  TCC  CCC  TAC  GTG  ACA  CAA  GGG  GGT
          920            930            940            950            960

321  E    M    T    L    N    K    L    S    Q    P    V    Q    H    P    S    E    336
     GAG  ATG  ACA  CTC  AAT  AAA  CTC  TCA  CAA  CCA  GTA  CAA  CAC  CCT  TCC  GAG
               970            980            990            1000

337  L    I    K    S    A    T    A    G    G    P    D    M    G    V    E    K    352
     TTA  ATT  AAA  TCT  GCC  ACA  GCG  GGC  GGA  CCT  GAT  ATG  GGA  GTG  GAA  AAG
     1010           1020           1030           1040           1050

353  D    T    V    R    A    L    I    T    S    R    P    M    H    P    S    S    368
     GAC  ACT  GTC  CGT  GCA  TTG  ATC  ACC  TCG  CGC  CCG  ATG  CAT  CCA  AGC  TCC
          1060           1070           1080           1090           1100

369  S    A    K    L    L    S    K    L    D    A    A    G    S    I    E    E    384
     TCA  GCT  AAG  CTC  CTG  AGT  AAG  CTG  GAT  GCA  GCC  GGG  TCG  ATT  GAA  GAG
          1110           1120           1130           1140           1150

385  I    R    K    I    K    R    L    A    L    N    G    *                        396
     ATC  AGA  AAG  ATC  AAG  CGC  CTT  GCA  CTA  AAT  GGC  TAA
          1160           1170           1180
```

A primary use of the nucleotides as defined above is for the creation of plasmids using recombinant DNA technologies. The resulting recombinant molecule can then be introduced into an appropriate host. The plasmids thus created can be used to encode NP and P proteins. For expression of the NP and P proteins, any of the common expression vectors, especially the bacterial vectors can be used. The usable bacterial hosts for the vectors include any of the conventional prokaryotic cells. In this invention, the bacterial host used was *Escherichia coli*. Accordingly, a further aspect of the present invention provides for a prokaryotic cell, such as for example a bacterial cell and in particular an *E. coli* cell containing the nucleotides as defined above for the production of NP and P proteins.

The NP and P proteins, produced using recombinant plasmids in accordance with the present invention, can be in the fusion or non-fusion forms. In accordance with the embodiment of the present invention, it provides a method for producing the fusion and non-fusion forms of both the NP and P proteins of NDV virus strain AF2240 in an *E. coli* system. The preferred method for producing the fusion and non-fusion forms of both the NP and P proteins of NDV virus strain AF2240 comprises culturing the transformed *E. coli* of the present invention on an appropriate medium to express the said nucleocapsid protein and phosphoprotein, and isolating and purifying the expressed fusion proteins from the cultures.

While the invention will now be described in connection with certain preferred embodiments in the following experiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

DETAILED DESCRIPTION OF THE INVENTION

The present invention was accomplished through the employment of the recombinant DNA techniques which comprises the amplification of the NP and P coding regions of NDV strain AF2240, the cloning of the genes into the expression vector, the production of the transformed *E. coli*, the cultivation of the transformant, the expression of the NP and P proteins and the purification of the expressed fusion proteins.

The NP and P coding regions of NDV strain AF2240 which had been cloned into the expression vector were prepared through reverse transcription-polymerase chain reaction (RT-PCR). Three primers were used for each gene, which consisted of one forward and two reverse primers as listed below:

For the Amplification of the NP Gene

```
NPf1 (20 mer): 5'-cct tct gcc aac atg tct tc -3'
               (Forward primer; SEQ ID NO: 5)

NPr1 (20 mer): 5'-tca ata ccc cca gtc ggt gt -3'
               (Reverse primer SEQ ID NO: 6)

NPr2 (18 mer): 5'-ata ccc cca gtc ggt gtc -3'
               (Reverse primer; SEQ ID NO: 7)
```

For the Amplification of the P Gene

```
Pf1 (20 mer): 5'-atg gcc acc ttt aca gat gc -3'
              (Forward primer; SEQ ID NO: 8)

Pr1 (23 mer): 5'-taa tta gcc att tag tgc aag gc -3'
              (Reverse primer; SEQ ID NO: 9)

Pr2 (21 mer): 5'-gcc att tag tgc aag gcg ctt -3'
              (Reverse primer; SEQ ID NO: 10)
```

Figure 1:
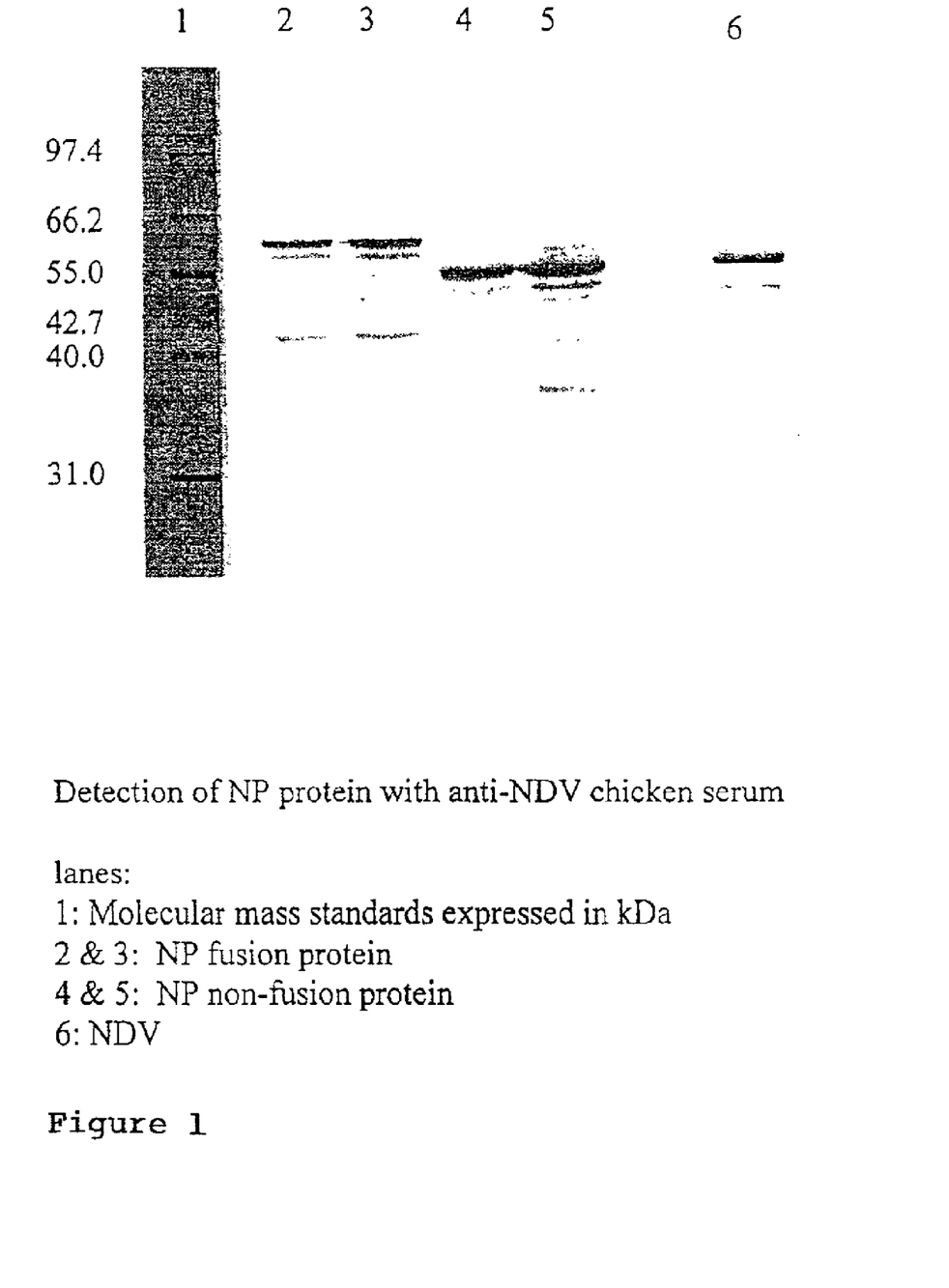
FIG. 1 is a western blot of NDV nucleocapsid protein (NP) expressed by transformed *E. coli* TOP10 containing plasmid pTrcHis2-NP
Figure 2:
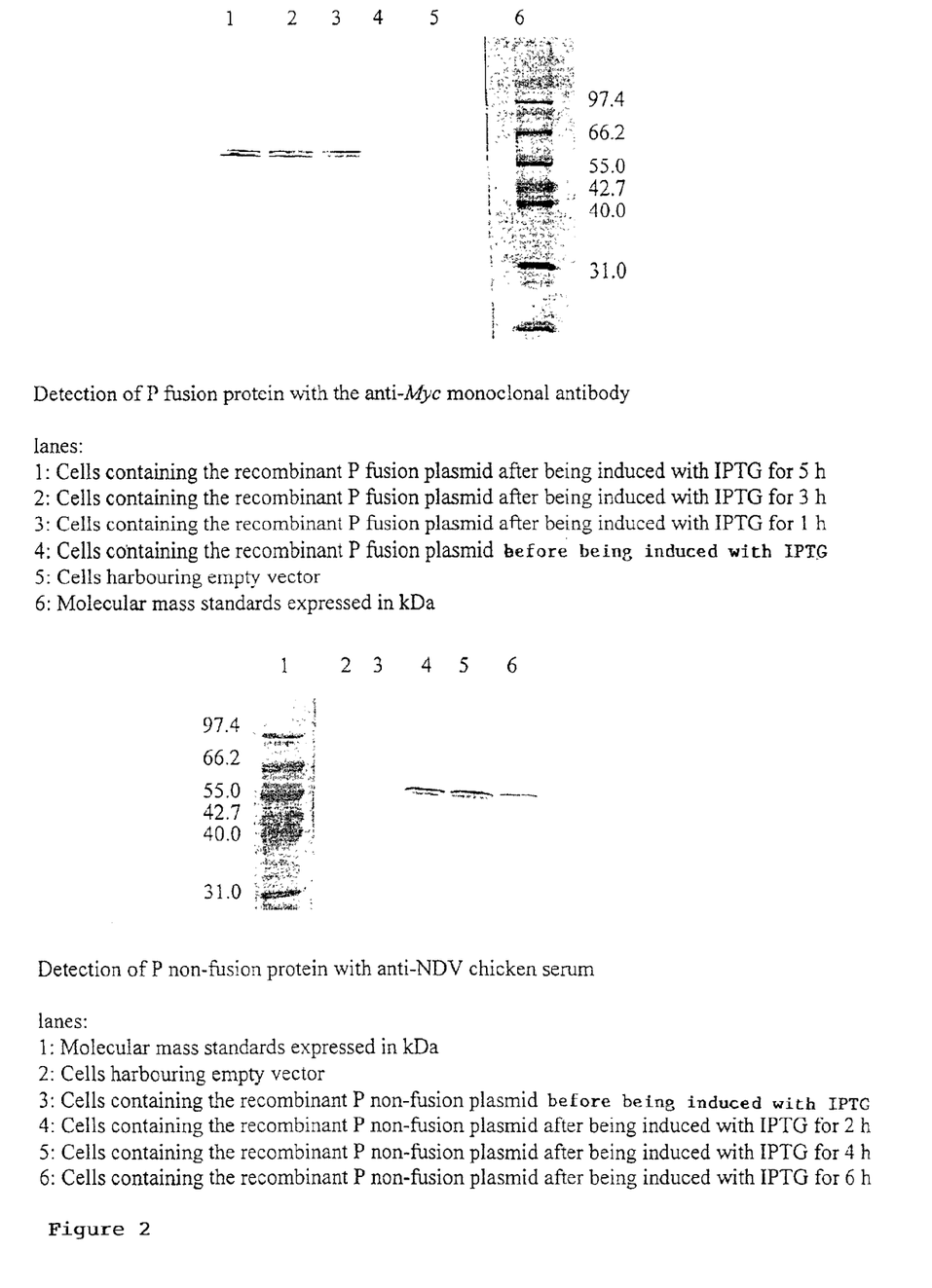
FIG. 2 is a western blot of NDV phosphoprotein (P) expressed by transformed *E. coli* TOP10 containing plasmid pTrcHis2-P

Incorporation of primers designated as NPf1 and NPr1 (for the NP gene), or Pf1 and Pr1 (for the P gene) during PCR had amplified gene products containing a stop codon at their 3' ends, while the presence of primers NPf1 and NPr2 (for the NP gene) or Pf1 and Pr2 (for the P gene) gave rise to genes without any no stop codon. For cloning and expression purposes, a commercially available expression vector, pTrcHis2 (Invitrogen, USA) containing the coding regions for the myc epitope and 6 His residues downstream of the multiple cloning site was used. After cloning of the respective coding regions of NP and P genes into the pTrcHis2 vector, they were subsequently introduced into a bacterial host *E. coli* TOP10. The resulting plasmid harbouring the NP gene was designated as pTrcHis2-NP while the other one with the P gene as an insert was denoted as pTrcHis2-P. Both the NP and P proteins were expressed in *E. coli* TOP10 cells as non-fusion and fusion proteins. The latter forms contain the myc epitope and 6 His residues at their C termini. For protein identification, protein samples were analysed with SDS-PAGE and then followed by immunoblotting with the anti-NDV chicken serum and the anti-myc monoclonal antibody. The western blots for NP and P proteins are as shown in FIG. 1 and FIG. 2, respectively.

The expressed NP fusion protein was purified with affinity chromatography (nickel column), and was judged to be more than 90% pure by SDS-PAGE.

The nucleotide sequences of the NP and P genes were determined by the ABI PRISM® automated sequencer, model 377. The recombinant plasmids, pTrcHis2-N and pTrcHis2-P, were used as templates and the synthetic primers used in the sequencing reactions of the NP and P genes are as follows:

For the Sequencing of the NP Gene Coding Region

```
pTrcHis2F      5'-gag gta tat att aat gta tcg -3'
(21 mer):      (SEQ ID NO: 11)

sNPf1 (21 mer): 5'-gac tca tac atc agg aac acc -3'
                (SEQ ID NO: 12)

sNPf2 (21 mer): 5'-gat gag agc agt ggc gaa cag -3'
                (SEQ ID NO: 13)

pTrcHis2R      5'-gat tta atc tgt atc agg -3'
(18 mer):      (SEQ ID NO: 14)

sNPr1 (20 mer): 5'-tca ata ccc cca gtc ggt gt -3'
                (SEQ ID NO: 15)

sNPr2 (21 mer): 5'-cta agt tgt aat acg tgg agc -3'
                (SEQ ID NO: 16)

sNPr3 (21 mer): 5'-cca tcg atc tca aga aca tgc -3'
                (SEQ ID NO: 17)
```

For the Sequencing of the P Gene Coding Region

```
pTrcHis2F      5'-gag gta tat att aat gta tcg -3'
(21 mer):      (SEQ ID NO: 18)

sPf (21 mer):  5'-gtc gac ttt gtg cag gcg atg -3'
               (SEQ ID NO: 19)

sPf2 (21 mer): 5'-gga cac tgt ccg tgc att gat -3'
               (SEQ ID NO: 20)

pTrcHis2.R     5'-gat tta atc tgt atc agg -3'
(18 mer):      (SEQ ID NO: 21)

sPr1 (21 mer): 5'-cca ggg tcc aga att ttc atc -3'
               (SEQ ID NO: 22)

sPr2 (22 mer): 5'-ggt gtg gat agc tgt ttg tct g -3'
               (SEQ ID NO: 23)
```

Both the NP and P coding regions were sequenced from 5' to 3' direction and reversely from 3' to 5' direction.

Example I illustrates the recombinant DNA techniques employed in obtaining bacterial clones harbouring a plasmid containing inserts of NP and P coding cDNA for NDV genomic RNA, the nucleotide sequences of the NP and P genes, and also the expressed NP and P proteins.

EXAMPLE I

Virus Propagation

The stock of NDV strain AF2240 was originally obtained from the Veterinary Research Institute (VRI), Ipoh. The virus was grown in the allantoic cavity of 8 to 9 day-old chicken embryonated eggs according to the procedures of Blaskovic and Styk (1967). After 3–4 days of incubation at 37° C., the eggs were chilled overnight at 4° C. The allantoic fluid was then harvested and the presence of the viruses was determined by haemagglutination (HA) test. The allantoic fluid which showed positive reaction of HA test was then clarified by centrifugation at 6000×g for 20 min at 4° C. (Beckman, JA14 rotor, USA) to remove debris.

Genomic RNA Extraction

Total RNA was extracted using the TRIZOL® LS reagent (Gibco BRL, USA). Briefly, 250 µl of the virus infected allantoic fluid was mixed with 750 µl Trizol LS reagent and incubated for 5 min at room temperature. After incubation, 100 µl of 1-bromo-3-chloropropane (BCP) (MRC, UK) was added and the mixtures were mixed vigorously for about 15 s and again incubated at room temperature for 10 min. The mixtures were base separated by microcentrifuging at 13,000×g for 15 min at 4° C. (Jouan MR 1812, France). The RNA was then precipitated by adding 500 μl of isopropanol (Merck) to the aqueous phase and left at room temperature for 10 min. The precipitated RNA was microcentrifuged at 13,000×g for 10 min and the pellet obtained was washed once with 75% (v/v) diethyl pyrocarbonate (DEPC) (Sigma, USA) treated ethanol (Hamburg). The pellet was dissolve in 20 μl of DEPC treated $dH_2O$.

cDNA Synthesis and Amplification of Nucleocapsid (NP) and Phosprotein (P) Genes by RT-PCR The amplification reactions were carried out in a programmed thermal cycler (MJ Research Inc. USA). Synthesis of the first strand cDNA was performed in a final volume of 30 μl. The reaction mixture contained 0.4 μM of each the forward and reverse primers, 0.2 mM deoxynucleoside triphosphate (MBI Fermentas, Inc. USA), 5 U of AMV reverse transcriptase (Promega, USA), 8 U of RNase inhibitor (Gibco BRL, USA), 1.5 mM of $MgCl_2$ and 1× of reaction buffer (50 mM Tris-HCl, 15 mM $(NH_4)_2SO_4$, 0.1% Triton X-100). The mixture was incubated at 42° C. for 30 min to synthesise the first strand of cDNA, and then 94° C. for 3 min to inactivate the reverse transcriptase.

For the amplification of the respective NP and P genes, another 20 μl of reaction mixture containing 1 U of DYNAZYME™ EXT DNA polymerase (FINNZYMES), 1.5 mM of $MgCl_2$ and 1× of reaction buffer was added to the top of the above cDNA mixture which was held at 94° C. in the thermal cycler. The PCR profile for the amplification of NP gene comprising denaturation at 94° C. for 30 s, annealing at 55° C. for 50 s and extension at 72° C. for 1 min for a total of 30 cycles. To ensure a complete synthesis of the PCR product, the extension step at 72° C. was prolonged for 7 min after the last cycle. The PCR profile for the amplification of P gene was basically similar to that of NP gene, except the annealing step was carried out at 55° C. for 30 s.

Purification of the Amplified PCR Products

A total of 40 μl of the amplified PCR product was analysed on 1% TAE agarose gel. After the staining with ethidium bromide, the band with the correct size was excised from the gel and purified with the WIZARD® PCR Preps DNA Purification System (Promega, USA) according to the manufacturer's procedures. After purification, 5 μl of the PCR product was again analysed with agarose gel electrophoresis to determine the recovery of the PCR product, which would be used in TA CLONING®.

TOP® TA Cloning of NP and P genes

Four μl of the purified NP or P DNA fragments carrying an A overhang at their 3' ends was mixed with 1 μl of the pTrcHis2 TOPO® expression vector (Invitrogen, USA) and the ligation reaction was carried out at room temperature (25° C.) for 5 min to form the desired recombinant plasmid.

Transformation

For transformation, 5 μl of the ligation mixture was added to 50 μl of TOP10 E. coli competent cells (Invitrogen, USA). The transformation mixture was incubated on ice for 30 min and the cells were heated at 42° C. for 30 to 60 s. This was followed by the adding of 250 μl SOC medium (2% trypton, 0.5% yeast extract, 10 mM NaCl, 2.5 mM KCl, 10 mM $MgCl_2$, 10 mM $MgSO_4$, 20 mM glucose) and the incubation of the reaction mixture at 37° C. for 30 to 60 min with shaking at 250 rpm. Thirty-50 μl of the transformation mixture was spread on a LB plate containing 50 μg/ml ampicillin and 0.5% of glucose, and the plates were then incubated overnight at 37° C.

Screening for Positive Clones

Ten single colonies were randomly chosen and cultured overnight in 3 to 5 ml of LB medium containing 50 μg/ml ampicillin and 0.5% glucose. Plasmid DNA was isolated by using the alkaline lysis method and the orientation of the insert in the positive clones was confirmed by PCR.

Protein Expression

The identified positive clones were cultured overnight in LB medium containing 50 μg/ml ampicillin. The next day, 10 ml of LB medium containing 50 μg/ml ampicillin was inoculated with 0.2 ml of the overnight culture and incubated at 37° C. with shaking at 250 rpm. Once the cells reached the optical density of 0.6 to 0.8 at $A_{600}$, 1 mM IPTG was added into the culture and continued shaking for 3 to 5 hours. The cells were harvested from the culture by centrifugation and then subjected to polyacrylamide gel electrophoresis (SDS-PAGE).

SDS-PAGE and Western Blotting

The cell pellets (from 1 ml culture solution) were resuspended in 50 to 100 μl of 1X SDS-PAGE sample buffer and boiled for 10 min. Five to 10 μl of the sample was loaded onto 12% SDS-PAGE gel and eletrophoresesed for 70 to 80 min at 32 volt. The proteins on SDS-PAGE gel were then electro-transferred onto a nitrocellulose membrane for 1 h. Western blotting was carried out by blocking the membrane first with skim milk for 1 h to saturate unoccupied regions on the membrane. This was followed by adding the anti-NDV chicken serum or anti-myc monoclonal antibody (for fusion protein) onto the membrane and this was shaken for 1 h at room temperature. The membrane was then washed four times with TTBS washing solution (TBS containing 0.5% Tween 20), 5 to 10 min for each wash to remove the unbound antibodies. After washing, peroxidase-labelled antibody was added to react with the primary antibody and left shaking for another 1 h. The membrane was further washed four times with TTBS solution, each for 5 to 10 min, and lastly BCIP/NBT solution was added as substrate for the peroxidase. The molecular weight of NP and P proteins was about 55 kDa while the fusion form for both the NP and P proteins gave rise to an apparent molecular weight of about 60 kDa.

Purification of NP Fusion Protein Using PROBOND™ Column Two hundred μl of LB medium containing 50 μg/ml ampicillin was cultured with 2 ml of overnight culture of transformant harbouring plasmid pTrcHis2-NP (carrying the NP insert without a stop codon), and the cells were grown to an $OD_{600}$ of 0.6 to 0.8. Protein expression was then induced by adding 1 mM IPTG and the cells were grown for another 5 h. The cells were harvested by centrifugation at 2000×g for 15 min at 4° C. The cell pellet was first resuspended in 10 ml of binding buffer (500 mM NaCl, 20 mM $NaH_2PO_4$, pH 7.8), then 100 μg/ml of lysozyme was added and incubated for 15 min on ice. The cells were lysed by sonication until the cell lysate is no longer viscous. The cell lysate was then treated with RNase and DNase I, both at a concentration of 5 μg/ml for 15 min at 30° C. The cell lysate was then centrifuged at 10,000×g for 20 min to remove all the cell debris. The supernatant was collected and p sed through a 0.45 μm filter. This cell lysate was incubated with the PROBOND™ resin (Invitrogen, USA) for 30 min and then allowed to drip through the resin. The column was washed with 10 ml of washing buffer (50 mM Imidazole, 500 mM NaCl, 20 mM $NaH_2PO_4$, pH 6.0), and the proteins were then eluted with 5 ml of elution buffer (500 mM Imidazole, 500 mM NaCl, 20 mM $NaH_2PO_4$, pH 6.0). The elute was collected as 1 ml fractions. Samples from each fractions were analysed on 12% SDS-PAGE to check the purity of the protein.

References

Abdul Rahman, M. S., Chee, Y. S. and Lim, S. S. (1976) Observation on the response of breeder flocks to ranikhet standard vaccination. Kajian Vet. 8: 48–53.

Blaskovic, D. and Stvk, B. (1967) Laboratory methods of virus transmission in multicellular organisms. In: Maramorasch, K. and Koprocvski, H. (Eds.), Virology, Vol. 1. Academic Press, New York, pp. 194–197.

Idris, Z., Yusoff, K. Shamaan, N. A. and Ibrahim, A. L. (1993) The Effect of temperature on different strains of Newcastle disease virus. 2$^{nd}$. UNESCO National Workshop on Promotion of Microbiology in Malaysia, 38.

Jemain S. F. P., (1999) Sequence determination of the Matrix gene in Newcastle disease virus strain AF2240. MS thesis, Universiti Putra Malaysia.

Lai C. M., (1985) A Study on a velogenic viscerotropic Newcastle disease virus in-vitro and in-vivo. PhD thesis, Universiti Pertanian Malaysia.

Salih, O., Omar, A. R., Ali, A. M. and Yusoff, K. (2000) Nucleotide sequence analysis of the F protein gene of a Malaysian velogenic NDV strain AF2240. Journal of Biochemistry, Molecular Biology and Biophysics 4: 51–57.

Tan, W. S., Lau, C. H., Ng, B. K., Ibrahim, A. L. and Yusoff, K. (1995) Nucleotide sequence of the haemagglutinin-neuraminidase (HN) gene of a Malaysian heat resistant viscerotropic-velogenic Newcastle disease virus (NDV) strain AF2240. DNA Sequence 6: 47–50.

What is claimed is:

1. An isolated nucleic acid molecule encoding the full-length nucleocapsid (NP) protein of Newcastle disease virus (NDV), wherein the full length nucleic acid molecule comprises the nucleotide sequence set forth as SEQ ID NO: 1.

2. A recombinant expression plasmid containing the isolated nucleic acid molecule as claimed in claim 1.

3. The recombinant expression plasmid according claim 2, wherein the expression plasmid comprises coding regions for a myc epitope and 6 His residues downstream of a multiple cloning site into which the isolated nucleic acid is inserted.

4. An *Escherichia coli* cell transformed with the recombinant expression plasmid of claim 2.

5. The *Escherichia coli* cell according to claim 4, which has a genotype of $F_{31}$ mcrA Δ(mrr-hsdRMS-mcrBC) φ80lacZΔM15ΔlacX74 recA1 araAΔ139 Δ(ara-leu)7697 galU galK rpsL ($Str^R$) endA1 nupG.

6. An *Escherichia coli* cell transformed with the recombinant expression plasmid of claim 3.

7. The *Escherichia coli* cell according to claim 6, which has a genotype of $F^{31}$ mcrA Δ(mrr-hsdRMS-mcrBC) φ80lacZΔM15 ΔlacX74 recA1 araAΔ139 Δ(ara-leu)7697 galU galK rpsL ($Str^R$) endA1 nupG.

* * * * *

UNITED STATES PATENT AND TRADEMARK OFFICE
CERTIFICATE OF CORRECTION

PATENT NO.         : 6,939,957 B2                                           Page 1 of 1
APPLICATION NO. : 09/970851
DATED              : September 6, 2005
INVENTOR(S)       : Yusoff et al.

It is certified that error appears in the above-identified patent and that said Letters Patent is hereby corrected as shown below:

In claim 1, column 29, line 31, please insert the word --to-- after the word "according" which should read:

--The recombinant expression plasmid according to claim--

In claim 5, column 30, line 31, please replace the symbol "$F_{31}$" with the symbol "$F^-$" which should read:

--has a genotype of $F^-$ mcr A $\Delta$(mrr-hsdRMS-mcrBC)--

In claim 5, column 30, line 32, please delete the symbol "A" directly after "ara" which should read:

--ara$\Delta$139--

In claim 7, column 30, line 37, please replace the symbol "$F_{31}$" with the symbol "$F^-$" which should read:

--has a genotype of $F^-$ mcr A $\Delta$(mrr-hsdRMS-mcrBC)--

Signed and Sealed this

Twenty-first Day of August, 2007

JON W. DUDAS
*Director of the United States Patent and Trademark Office*

SEQUENCE LISTING

<160> NUMBER OF SEQ ID NOS: 23

<210> SEQ ID NO 1
<211> LENGTH: 1470
<212> TYPE: DNA
<213> ORGANISM: Newcastle disease virus

<400> SEQUENCE: 1

```
atgtcttccg tattcgatga atacgagcag ctcctcgctg ctcagactcg ccccaatgga      60
gctcacggag ggggagagag agggagcact ttaagagttg aggtcccagt attcactctt     120
aacagtgacg atccagaaga tagatggaat tttgcggtat tctgtcttcg gattgctgtt     180
agcgaggacg ccaacaaacc gctcaggcaa ggtgctctca tatccctcct gtgctcccat     240
tctcaagtga tgaggaacca tgttgccctt gcaggaaaac agaatgaggc tacactgact     300
gttcttgaga tcgatggttt taccagcagc gtgcctcagt tcaacaacag gagtggggtg     360
tctgaggaga gagcacagag attcatggtg atagcagggt ctctccctcg ggcgtgcagt     420
aacggtactc cgttcgtcac ggctggggtt gaagatgatg caccagaaga tatcactgat     480
actctggaaa gaatcctgtc tatccaggct caggtatggg tcacagtagc gaaggccatg     540
actgcatatg agacagcaga tgagtcggaa acaagaagaa tcaataagta catgcagcaa     600
ggcagagtcc agaagaagta catcctccac cctgtatgca ggagtgcaat tcaactcaca     660
atcagacatt ctctggcagt ccgcattttc ttagttagcg agcttaagag aggccgcaat     720
acggcaggtg ggagctccac gtattacaac ttagtagggg atgtagactc atacatcagg     780
aacaccggac ttactgcatt cttccttaca ctcaaatatg gaattaatac caagacatca     840
gccctagcac tcagcagcct cacaggcgat atccaaaaga tgaagcagct catgcgttta     900
tatcggatga agggagaaaa tgcgccgtac atgacattgc taggtgacag tgatcagatg     960
agctttgcac cggctgagta tgcacagctt tattcttttg ccatgggcat ggcatcagtc    1020
ttagataaag gaactggcaa ataccaattc gccagagact tcatgagcac atcattctgg    1080
agactcgggg tggagtatgc tcaggctcag gggagtagca tcaacgaaga catggctgct    1140
gagctaaaac taacccccggc agcaagaagg ggcctggcag ctgctgccca acgagtgtct    1200
gaggaaactg gcagcgtgga tattcctact caacaagccg gggtcctcac tgggctcagc    1260
gatggaggcc cccgagcctc tcagggtgga tcgaacaagt cgcaagggca accagatgcc    1320
ggagatgggg agacccaatt cttggatttg atgagagcag tggcgaacag catgcgagaa    1380
gcgccaaact ccgcacagag caccacccac ccggaacccc ccccgactcc cgggccatca    1440
caagataacg acaccgactg ggggtattga                                     1470
```

<210> SEQ ID NO 2
<211> LENGTH: 1188
<212> TYPE: DNA
<213> ORGANISM: Newcastle disease virus

<400> SEQUENCE: 2

| | | | | | |
|---|---|---|---|---|---|
| atggccacct | ttacagatgc | ggagatagat | gatatatttg | agaccagtgg | aactgtcatt | 60 |
| gacagcataa | ttacggccca | gggtaaatca | gcagagactg | tcggaaggag | cgcaatccca | 120 |
| caaggcaaga | ccaaagcgct | gagcatagca | tgggagaagc | atgggagcat | ccaaccatcc | 180 |
| accagccagg | acaaccccga | ccaacaggat | agaccagaca | acagctatc | cacacctgag | 240 |
| caggcgaccc | cacacaacag | ctcgccagcc | acatccgccg | aaccgctccc | cactcaggcc | 300 |
| gcaggtgagg | ccggcgacac | acagctcaag | accggagcaa | gcaactctct | tctgtctatg | 360 |
| ctcgacaagc | tgagcaataa | accatctaat | gctaaaaagg | gcccatggtc | gagtccccag | 420 |
| gaaggatatc | atcaacctcc | gacccaacaa | catggggatc | agccgaaccg | cggaaacagc | 480 |
| caggagaggc | tgcggcacca | gccaaggcc | gcccctggaa | gccggggcac | agacgcgagc | 540 |
| acagcatatc | atggacaatg | gaaggagtca | caactatcag | ctggtgcaac | ccctcatgtg | 600 |
| ctccaatcag | ggcagagcca | agacagtact | cctgtacctg | tggatcatgt | ccagccacct | 660 |
| gtcgactttg | tgcaggcgat | gatgactatg | atggaggcgt | tatcacagaa | ggtaagtaaa | 720 |
| gtcgactatc | agctagacct | agtcttaaag | cagacatcct | ccatccctat | gatgcggtct | 780 |
| gaaatccaac | agctaaaaac | atctgttgcg | gtcatggaag | ctaatttagg | catgatgaaa | 840 |
| attctggacc | ctggttgtgc | taacatttca | tccttaagtg | atctgcgggc | agtcgcccgg | 900 |
| tcccacccag | ttttaatttc | aggccccgga | gatccgtccc | cctacgtgac | acaaggggt | 960 |
| gagatgacac | tcaataaact | ctcacaacca | gtacaacacc | cttccgagtt | aattaaatct | 1020 |
| gccacagcgg | gcggacctga | tatgggagtg | gaaaaggaca | ctgtccgtgc | attgatcacc | 1080 |
| tcgcgcccga | tgcatccaag | ctcctcagct | aagctcctga | gtaagctgga | tgcagccggg | 1140 |
| tcgattgaag | agatcagaaa | gatcaagcgc | cttgcactaa | atggctaa | | 1188 |

<210> SEQ ID NO 3
<211> LENGTH: 489
<212> TYPE: PRT
<213> ORGANISM: Newcastle disease virus

<400> SEQUENCE: 3

Met Ser Ser Val Phe Asp Glu Tyr Glu Gln Leu Leu Ala Ala Gln Thr
1               5                   10                  15

Arg Pro Asn Gly Ala His Gly Gly Glu Arg Gly Ser Thr Leu Arg
            20                  25                  30

Val Glu Val Pro Val Phe Thr Leu Asn Ser Asp Asp Pro Glu Asp Arg
        35                  40                  45

Trp Asn Phe Ala Val Phe Cys Leu Arg Ile Ala Val Ser Glu Asp Ala
    50                  55                  60

Asn Lys Pro Leu Arg Gln Gly Ala Leu Ile Ser Leu Cys Ser His
65                  70                  75                  80

Ser Gln Val Met Arg Asn His Val Ala Leu Ala Gly Lys Gln Asn Glu
                85                  90                  95

Ala Thr Leu Thr Val Leu Glu Ile Asp Gly Phe Thr Ser Ser Val Pro
            100                 105                 110

```
Gln Phe Asn Asn Arg Ser Gly Val Ser Glu Arg Ala Gln Arg Phe
            115                 120                 125

Met Val Ile Ala Gly Ser Leu Pro Arg Ala Cys Ser Asn Gly Thr Pro
    130                 135                 140

Phe Val Thr Ala Gly Val Glu Asp Asp Ala Pro Glu Asp Ile Thr Asp
145                 150                 155                 160

Thr Leu Glu Arg Ile Leu Ser Ile Gln Ala Gln Val Trp Val Thr Val
                165                 170                 175

Ala Lys Ala Met Thr Ala Tyr Glu Thr Ala Asp Glu Ser Glu Thr Arg
            180                 185                 190

Arg Ile Asn Lys Tyr Met Gln Gln Gly Arg Val Gln Lys Lys Tyr Ile
        195                 200                 205

Leu His Pro Val Cys Arg Ser Ala Ile Gln Leu Thr Ile Arg His Ser
    210                 215                 220

Leu Ala Val Arg Ile Phe Leu Val Ser Glu Leu Lys Arg Gly Arg Asn
225                 230                 235                 240

Thr Ala Gly Gly Ser Ser Thr Tyr Tyr Asn Leu Val Gly Asp Val Asp
                245                 250                 255

Ser Tyr Ile Arg Asn Thr Gly Leu Thr Ala Phe Phe Leu Thr Leu Lys
            260                 265                 270

Tyr Gly Ile Asn Thr Lys Thr Ser Ala Leu Ala Leu Ser Ser Leu Thr
        275                 280                 285

Gly Asp Ile Gln Lys Met Lys Gln Leu Met Arg Leu Tyr Arg Met Lys
    290                 295                 300

Gly Glu Asn Ala Pro Tyr Met Thr Leu Leu Gly Asp Ser Asp Gln Met
305                 310                 315                 320

Ser Phe Ala Pro Ala Glu Tyr Ala Gln Leu Tyr Ser Phe Ala Met Gly
                325                 330                 335

Met Ala Ser Val Leu Asp Lys Gly Thr Gly Lys Tyr Gln Phe Ala Arg
            340                 345                 350

Asp Phe Met Ser Thr Ser Phe Trp Arg Leu Gly Val Glu Tyr Ala Gln
        355                 360                 365

Ala Gln Gly Ser Ser Ile Asn Glu Asp Met Ala Ala Glu Leu Lys Leu
    370                 375                 380

Thr Pro Ala Ala Arg Arg Gly Leu Ala Ala Ala Gln Arg Val Ser
385                 390                 395                 400

Glu Glu Thr Gly Ser Val Asp Ile Pro Thr Gln Gln Ala Gly Val Leu
                405                 410                 415

Thr Gly Leu Ser Asp Gly Gly Pro Arg Ala Ser Gln Gly Gly Ser Asn
            420                 425                 430

Lys Ser Gln Gly Gln Pro Asp Ala Gly Asp Gly Glu Thr Gln Phe Leu
        435                 440                 445

Asp Leu Met Arg Ala Val Ala Asn Ser Met Arg Glu Ala Pro Asn Ser
    450                 455                 460

Ala Gln Ser Thr Thr His Pro Glu Pro Pro Thr Pro Gly Pro Ser
465                 470                 475                 480

Gln Asp Asn Asp Thr Asp Trp Gly Tyr
                485

<210> SEQ ID NO 4
<211> LENGTH: 395
<212> TYPE: PRT
<213> ORGANISM: Newcastle disease virus
```

-continued

```
<400> SEQUENCE: 4

Met Ala Thr Phe Thr Asp Ala Glu Ile Asp Ile Phe Glu Thr Ser
1               5                   10                  15

Gly Thr Val Ile Asp Ser Ile Ile Thr Ala Gln Gly Lys Ser Ala Glu
            20                  25                  30

Thr Val Gly Arg Ser Ala Ile Pro Gln Gly Lys Thr Lys Ala Leu Ser
            35                  40                  45

Ile Ala Trp Glu Lys His Gly Ser Ile Gln Pro Ser Thr Ser Gln Asp
    50                  55                  60

Asn Pro Asp Gln Gln Asp Arg Pro Asp Lys Gln Leu Ser Thr Pro Glu
65                  70                  75                  80

Gln Ala Thr Pro His Asn Ser Ser Pro Ala Thr Ser Ala Glu Pro Leu
                85                  90                  95

Pro Thr Gln Ala Ala Gly Glu Ala Gly Asp Thr Gln Leu Lys Thr Gly
                100                 105                 110

Ala Ser Asn Ser Leu Leu Ser Met Leu Asp Lys Leu Ser Asn Lys Pro
            115                 120                 125

Ser Asn Ala Lys Lys Gly Pro Trp Ser Ser Pro Gln Glu Gly Tyr His
            130                 135                 140

Gln Pro Pro Thr Gln Gln His Gly Asp Gln Pro Asn Arg Gly Asn Ser
145                 150                 155                 160

Gln Glu Arg Leu Arg His Gln Ala Lys Ala Ala Pro Gly Ser Arg Gly
                165                 170                 175

Thr Asp Ala Ser Thr Ala Tyr His Gly Gln Trp Lys Glu Ser Gln Leu
            180                 185                 190

Ser Ala Gly Ala Thr Pro His Val Leu Gln Ser Gly Gln Ser Gln Asp
            195                 200                 205

Ser Thr Pro Val Pro Val Asp His Val Gln Pro Val Asp Phe Val
210                 215                 220

Gln Ala Met Met Thr Met Met Glu Ala Leu Ser Gln Lys Val Ser Lys
225                 230                 235                 240

Val Asp Tyr Gln Leu Asp Leu Val Leu Lys Gln Thr Ser Ser Ile Pro
                245                 250                 255

Met Met Arg Ser Glu Ile Gln Gln Leu Lys Thr Ser Val Ala Val Met
            260                 265                 270

Glu Ala Asn Leu Gly Met Met Lys Ile Leu Asp Pro Gly Cys Ala Asn
            275                 280                 285

Ile Ser Ser Leu Ser Asp Leu Arg Ala Val Ala Arg Ser His Pro Val
    290                 295                 300

Leu Ile Ser Gly Pro Gly Asp Pro Ser Pro Tyr Val Thr Gln Gly Gly
305                 310                 315                 320

Glu Met Thr Leu Asn Lys Leu Ser Gln Pro Val Gln His Pro Ser Glu
                325                 330                 335

Leu Ile Lys Ser Ala Thr Ala Gly Gly Pro Asp Met Gly Val Glu Lys
                340                 345                 350

Asp Thr Val Arg Ala Leu Ile Thr Ser Arg Pro Met His Pro Ser Ser
            355                 360                 365

Ser Ala Lys Leu Leu Ser Lys Leu Asp Ala Ala Gly Ser Ile Glu Glu
            370                 375                 380

Ile Arg Lys Ile Lys Arg Leu Ala Leu Asn Gly
385                 390                 395
```

```
<210> SEQ ID NO 5
<211> LENGTH: 20
<212> TYPE: DNA
<213> ORGANISM: Newcastle disease virus

<400> SEQUENCE: 5
ccttctgcca acatgtcttc                                                     20

<210> SEQ ID NO 6
<211> LENGTH: 20
<212> TYPE: DNA
<213> ORGANISM: Newcastle disease virus

<400> SEQUENCE: 6 tcaataccccc cagtcggtgt                                                    20

<210> SEQ ID NO 7
<211> LENGTH: 18
<212> TYPE: DNA
<213> ORGANISM: Newcastle disease virus

<400> SEQUENCE: 7 ataccccag tcggtgtc                                                        18

<210> SEQ ID NO 8
<211> LENGTH: 20
<212> TYPE: DNA
<213> ORGANISM: Newcastle disease virus

<400> SEQUENCE: 8
atggccacct ttacagatgc                                                     20

<210> SEQ ID NO 9
<211> LENGTH: 23
<212> TYPE: DNA
<213> ORGANISM: Newcastle disease virus

<400> SEQUENCE: 9
taattagcca tttagtgcaa ggc                                                 23

<210> SEQ ID NO 10
<211> LENGTH: 21
<212> TYPE: DNA
<213> ORGANISM: Newcastle disease virus

<400> SEQUENCE: 10
gccatttagt gcaaggcgct t                                                   21

<210> SEQ ID NO 11
<211> LENGTH: 21
<212> TYPE: DNA
<213> ORGANISM: Newcastle disease virus

<400> SEQUENCE: 11
gaggtatata ttaatgtatc g                                                   21

<210> SEQ ID NO 12
<211> LENGTH: 21
<212> TYPE: DNA
<213> ORGANISM: Newcastle disease virus

<400> SEQUENCE: 12
gactcataca tcaggaacac c                                                   21
```

```
<210> SEQ ID NO 13
<211> LENGTH: 21
<212> TYPE: DNA
<213> ORGANISM: Newcastle disease virus

<400> SEQUENCE: 13
gatgagagca gtggcgaaca g                                      21

<210> SEQ ID NO 14
<211> LENGTH: 18
<212> TYPE: DNA
<213> ORGANISM: Newcastle disease virus

<400> SEQUENCE: 14
gatttaatct gtatcagg                                          18

<210> SEQ ID NO 15
<211> LENGTH: 20
<212> TYPE: DNA
<213> ORGANISM: Newcastle disease virus

<400> SEQUENCE: 15 tcaataccc cagtcggtgt                                         20

<210> SEQ ID NO 16
<211> LENGTH: 21
<212> TYPE: DNA
<213> ORGANISM: Newcastle disease virus

<400> SEQUENCE: 16
ctaagttgta atacgtggag c                                      21

<210> SEQ ID NO 17
<211> LENGTH: 21
<212> TYPE: DNA
<213> ORGANISM: Newcastle disease virus

<400> SEQUENCE: 17
ccatcgatct caagaacatg c                                      21

<210> SEQ ID NO 18
<211> LENGTH: 21
<212> TYPE: DNA
<213> ORGANISM: Newcastle disease virus

<400> SEQUENCE: 18
gaggtatata ttaatgtatc g                                      21

<210> SEQ ID NO 19
<211> LENGTH: 21
<212> TYPE: DNA
<213> ORGANISM: Newcastle disease virus

<400> SEQUENCE: 19
gtcgactttg tgcaggcgat g                                      21

<210> SEQ ID NO 20
<211> LENGTH: 21
<212> TYPE: DNA
<213> ORGANISM: Newcastle disease virus

<400> SEQUENCE: 20
ggacactgtc cgtgcattga t                                      21
```

```
<210> SEQ ID NO 21
<211> LENGTH: 18
<212> TYPE: DNA
<213> ORGANISM: Newcastle disease virus

<400> SEQUENCE: 21
gatttaatct gtatcagg                                         18

<210> SEQ ID NO 22
<211> LENGTH: 21
<212> TYPE: DNA
<213> ORGANISM: Newcastle disease virus

<400> SEQUENCE: 22
ccagggtcca gaattttcat c                                     21

<210> SEQ ID NO 23
<211> LENGTH: 22
<212> TYPE: DNA
<213> ORGANISM: Newcastle disease virus

<400> SEQUENCE: 23
ggtgtggata gctgtttgtc tg                                    22
```